United States Patent [19]
Kuwabara et al.

[11] Patent Number: 5,321,264
[45] Date of Patent: Jun. 14, 1994

[54] METHOD FOR EVALUATING SURFACE STATE OF SILICON WAFER

[75] Inventors: Susumu Kuwabara; Takao Abe, both of Annaka, Japan

[73] Assignee: Shin-Etsu Handotai Co., Ltd., Tokyo, Japan

[21] Appl. No.: 914,625

[22] Filed: Jul. 20, 1992

[30] Foreign Application Priority Data

Jul. 23, 1991 [JP] Japan .................. 3-205720

[51] Int. Cl.$^5$ .................................. G01J 3/42
[52] U.S. Cl. ................... 250/339.01; 356/244
[58] Field of Search ............. 250/339, 341; 356/244

[56] References Cited
U.S. PATENT DOCUMENTS

| | | | |
|---|---|---|---|
| 3,850,508 | 11/1974 | Sittig et al. | 356/209 |
| 4,211,488 | 7/1980 | Kleinknecht | 356/369 |
| 4,291,990 | 9/1981 | Takasu | 356/445 |
| 4,352,016 | 9/1982 | Duffy et al. | 250/358.1 |
| 4,468,136 | 8/1984 | Murphy et al. | 374/45 |
| 4,547,073 | 10/1985 | Kugimiya | 356/371 |
| 4,652,757 | 3/1987 | Carver | 250/360.1 |
| 4,862,000 | 8/1989 | Kubota et al. | 250/341 |
| 4,953,983 | 9/1990 | Bottka et al. | 356/445 |
| 5,042,952 | 8/1991 | Opsal et al. | 356/432 |
| 5,185,640 | 2/1993 | Wilks, Jr. et al. | 250/339 |
| 5,214,286 | 5/1993 | Milosevic et al. | 250/339 |

FOREIGN PATENT DOCUMENTS 63-157434  6/1988  Japan .
63-302347 12/1988  Japan .

OTHER PUBLICATIONS

*Japanese Journal of Applied Physics*, vol. 27, No. 8 (Aug. 1988).
*Journal of Applied Physics*, vol. 64, No. 7 (Oct. 1988).
*Journal of Applied Physics*, vol. 66, No. 3 (Aug. 1989).
*Applied Physics Letters*, vol. 53, No. 20 (Nov. 1988).
*Applied Physics Letters*, vol. 56, No. 7 (Feb. 1990).
*Physical Review B-Condensed Matter*, vol. 42, No. 11, Third Series (Oct. 1990).

Primary Examiner—Paul M. Dzierzynski
Assistant Examiner—Richard Hanig
Attorney, Agent, or Firm—Evenson, McKeown, Edwards & Lenahan

[57] ABSTRACT

A method for evaluating the surface state of a silicon wafer is here disclosed which comprises the steps of directly bringing an internal reflection element having a larger refractive index than that of silicon into close contact with the surface of the silicon wafer, selecting a light source having a wave length range which compounds present on the surface can absorb, entering light having a larger incident angle than critical angle from the light source into the element, and then evaluating a chemical bond state on the surface containing impurities or impure atoms by means of a multi-reflection method.

8 Claims, 7 Drawing Sheets

METHOD FOR EVALUATING SURFACE STATE OF SILICON WAFER

BACKGROUND OF THE INVENTION (i) Field of the Invention

The present invention relates to a method for evaluating the surface state of a polished silicon wafer, and more specifically it relates to a method for evaluating the terminal bond state of different kinds of atoms on the surface of a silicon wafer, a natural oxide film, or molecular pollutants adhered onto the wafer surface in accordance with a multi-internal reflection method.

(ii) Description of the Prior Art

Heretofore, for the elemental analysis of the surface of a substance, there can be utilized, for example, an X-ray microanalyzer which comprises irradiating a sample with electron beams, and an ion micro-analyzer which comprises irradiating the sample with ion beams. According to these techniques, the kinds of elements on the surface and the structure of the surface can not be analyzed without destroying the surface.

Furthermore, another multi-internal reflection method has been suggested by Takahagi et al. in which silicon crystal itself is used as an internal reflection element and an incident angle is larger than a critical angle [T. Takahagi, I. Nagai, A. Ishitani, H. Kuroda, and Y. Nagasawa, J. Appln. Phys., 64, 3516 (1988)], and they have reported on the bond state of the different kinds of atoms on the silicon surface being an Si-H bond and the oxidation process of the surface.

However, in most cases of these analytical methods of applying the certain kind of beams, the sample must be disposed in vacuo, and a chemical bond on the surface may be destroyed on occasion, depending upon the energy of the beams. Thus, some restriction has been put on these techniques.

Additionally, in the multi-internal reflection method suggested by Takahagi et al. in which silicon itself is used as the internal reflection element, this internal reflection element as a reference must have a chemically clean silicon surface and this surface state must be well known. Accordingly, it has been substantially impossible to directly evaluate the surface of the silicon wafer.

FIG. 7 is a spectrum drawing obtained by measuring an oxide film on the silicon surface in accordance with an infrared multi-internal reflection method in which the silicon crystal is used as the internal reflection element. The transmittable wave length range of silicon extend from 1.1 to 6 $\mu$m (9,100 to 1,700 cm$^{-1}$), and therefore the measurement is possible in the wave length range of about 2,000 cm$^{-1}$ or more, but chemical species having absorption bands at wave-numbers (1/wave length less than the wave numbers can not be observed.

However, it is necessary to directly evaluate the surface of the silicon wafer from the viewpoint of controlling a wafer manufacturing process. For example, a washing treatment step with a hydrofluoric acid solution is a pretreatment step for a silicon device process such as a thermal oxidation step or an epitaxial growth step, and it is strongly desired from the viewpoint of the process control to evaluate the wafer surface treated in this step.

SUMMARY OF THE INVENTION

For the solution of the above-mentioned technical problems, an object of the present invention is to provide a method for simply and directly evaluating/analyzing light elements, i.e., chemical impurities such as water, hydrocarbons and amines adhering to the surface of a polished silicon wafer in the atmosphere with a high sensitivity without requiring vacuum.

Another object of the present invention is to provide a method for simply evaluating/analyzing a natural oxide film, a surface bond state and a surface smoothness on an atomic level on the surface of a polished silicon wafer in the atmosphere with a high sensitivity without requiring vacuum.

Other objects of the present invention will be apparent from the description of the function and examples of the present invention which will be given hereinafter.

Thus, the present invention comprises the steps of directly bringing an internal reflection element having a large refractive index than that of silicon into close contact with the surface to be measured of a silicon wafer;

selecting a light source having a wave length range which compounds present on the surface to be measured can absorb, introducing the light having a larger incident angle than a critical angle from the light source into the element, and then evaluating a chemical bond state on the surface to be measured in accordance with a multi-reflection method.

Furthermore, the employment of germanium as the internal reflection element permits achieving the preferable evaluation.

Next, the present invention will be described in more detail mainly with regard to its function.

In the first place, silicon is brought into close contact with the internal reflection element having a larger refractive index ni than that ns of silicon, and a light beam is introduced from an internal reflection element side to a silicon side at an angle of $\theta i$ to a boundary normal. In this case, the Snell's law can be represented by $$n_i \sin \theta i = n_s \sin \theta s \quad \text{(Formula 1)}$$

wherein s is a refractive angle to the same normal of the light beam transmitted to the silicon side.

Here, $$\sin \theta s = 1 \quad \text{(Formula 2)}$$

That is, in the case of sin $\theta s = 90°$, the light beam entered through the element cannot transmit through silicon because of the refractive angle being 90°, so that the beam is all reflected.

In the case of sin $\theta s = 90°$, the formula 1 can be converted into the following formula 1'.

$$\sin \theta i(\theta s = 90°) = (n_s/n_i) \quad \text{(Formula 1')}$$

Here, sin $\theta i(\theta s = 90°)$ is defined as sin $\theta$.

This $\theta i(\theta s = 90°)$ is called a critical angle $\theta c$, and the light beam entered at an angle $\theta i$, ref more than the critical angle $\theta c$ and less than 90°

$$\{\theta c < \theta i, \text{ref} < 90°\}$$

is all reflected.

If a compound such as the natural oxide film is present on the surface of the silicon wafer on the side of an interface between the internal reflection element and the silicon wafer, the reflected light of the light beam in the interface has an absorption band inherent in the compound, so that some extinction from the total reflection takes place. Thus, the above-mentioned compound can be identified by spectral analysis.

Additionally, in the case that the silicon wafer is observed by the multi-internal reflection method in which silicon itself is used as the internal reflection element, this internal reflection element as a reference must have a chemically and physically clean silicon surface and this surface state must be well known. According to the present invention, however, a substance other than silicon is utilized as the internal reflection element, and so a relative absorbance to a blank measurement is obtained and used to offset the same. Therefore, so long as the surface state of the element is stable, attention does not have to be particularly paid to the surface state.

Furthermore, comparing spectrograms of vertical polarized light and parallel polarized light, amounts of SiH, $SiH_2$ and $SiH_3$ produced by a treatment with an HF solution can be represented as spectral intensities in the vicinity of atomic steps, whereby the information regarding the roughness on a micro level on the surface of the silicon wafer can be obtained.

According to the present invention, the evaluation/measurement can be made by bringing a prism element, for example, comprising germanium crystal or another internal reflection element into close contact with the surface of the silicon wafer, and in other words, the surface of the silicon wafer is airtightly sealed with the internal reflection element. Therefore, even if the silicon wafer is directly exposed to the atmosphere at the time of the evaluation/measurement, the wafer surface is not contaminated with impurities or chemical pollutants, and the silicon wafer itself is not handled as the internal reflection element but as the material to be measured. In consequence, the evaluation/measurement can be achieved directly in the atmosphere, and a change of the wafer surface state which tends to occur in vacuo can be prevented, so that the high quality of the silicon wafer can be easily maintained.

Moreover, since the surface of the silicon wafer is concealed with the internal reflection element, the wafer surface state immediately after contamination by handling, washing or another process can be evaluated with a high sensitivity, whereby such a process can be easily controlled.

According to the present invention, germanium is used as the internal reflection element, and therefore a transmittable wave length range extends to a long wave length range and it is from 2.5 to 14 μm (wave number=4,000 to 700 $cm^{-1}$). On the other hand, in the case that silicon is used as the element, the transmittable wave length range is from 1.1 to 6 μm (wave-number=9,100 to 1,700 $cm^{-1}$). In consequence, the present invention permits measuring chemical species such as SiF, $SiF_2$, $SiH_2$, $O-(CH_3)_2Si-O$, $SiO_2$, $CH_2$, $CH_3$, water (OH) and amines of $RNH_2$ and RR 'NH which have not been measured so far.

According to the present invention, the measurement can be made by the total reflected light which has been absorbed and extinguished on the surface of the material to be measured, and therefore extremely thin oxide films such as a natural oxide film and a thermal oxide film formed on the silicon wafer surface can be evaluated.

Furthermore, according to the present invention, the measurement is made by the total reflected light on the surface of the material to be measured, and therefore the smoothness on an atomic level of the silicon wafer washed with a hydrofluoric acid solution can be simply evaluated in the atmosphere.

DETAILED DESCRIPTION OF THE PREFERRED EMBODIMENT

Now, the present invention will be described in more detail in reference to examples on the basis of drawings. However, size, material, shape and relative arrangement of constitutional parts referred to in the experimental examples do not intend to limit the scope of the present invention thereto, and they are only exemplary, unless otherwise specified.

Prior to the description of the constitution of the apparatus regarding the present invention, reference will be made to constitution of the main parts of the apparatus.

Figure 1A:
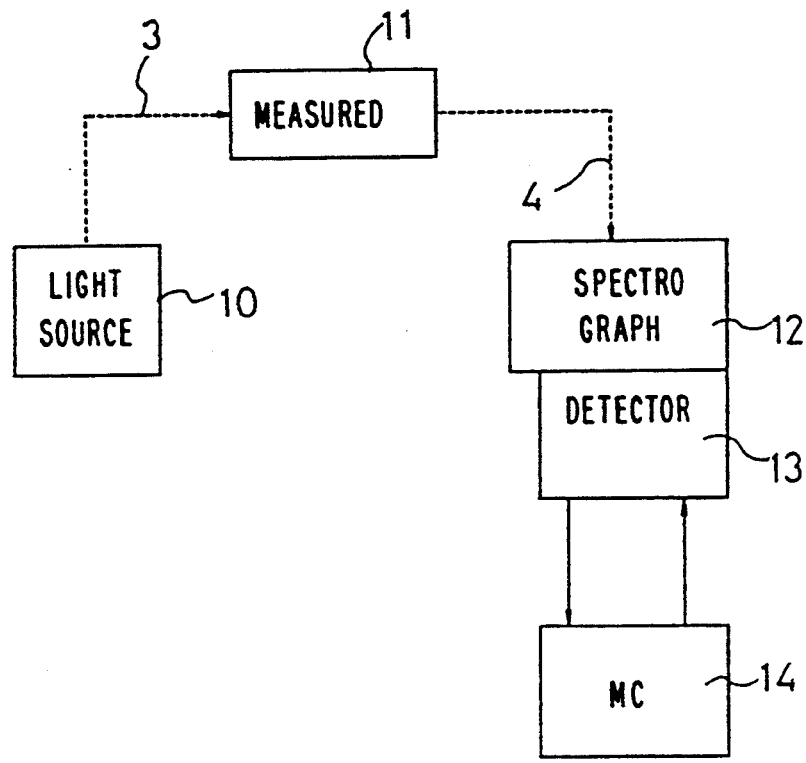
FIG. 1(A) shows a conceptual view of an apparatus for measuring the surface state of a silicon wafer regarding the present invention.

FIG. 1(A) shows a conceptual view of an apparatus for measuring the surface state of a silicon wafer in an example regarding the present invention, and this apparatus comprises a light source 10 for feeding infrared ray 3, a portion to be measured 11 for multiply reflecting the incident infrared ray 3 therein and outputting the undermentioned radiant infrared ray, a spectrograph 12 for separating the radiant infrared ray output from the portion to be measured 11, an MCT type detector 13 for calculating photons separated by the spectrograph 12 and then converting the photon number into a corresponding electrical signal, and a microcomputer 14 for Fourier-converting a detection output from the detector 13 into a spectral line, making a spectrum, and then controlling the whole apparatus.

As the light source 10, there is used what can output the wave-number (4,000–700 $cm^{-1}$) corresponding to 2.5–14 μm which is the transmittable wave length range of germanium.

The above-mentioned MCT type detector 13 is composed of a semi-conductor type detector in which mercury-cadmium-tellurium alloy having a good thermal response is used as an element.

As the spectrograph 12, there can be used, for example, a Fourier-conversion type infrared spectrograph FTS-40 made by Bio-Rad Co., Ltd., and it can be constituted so that 256 scans per measurement step may be carried out in compliance with a high response speed of the above-mentioned MCT type detector 13. The resolution of the spectrograph 12 is about 4 $cm^{-1}$.

Figure 1B:
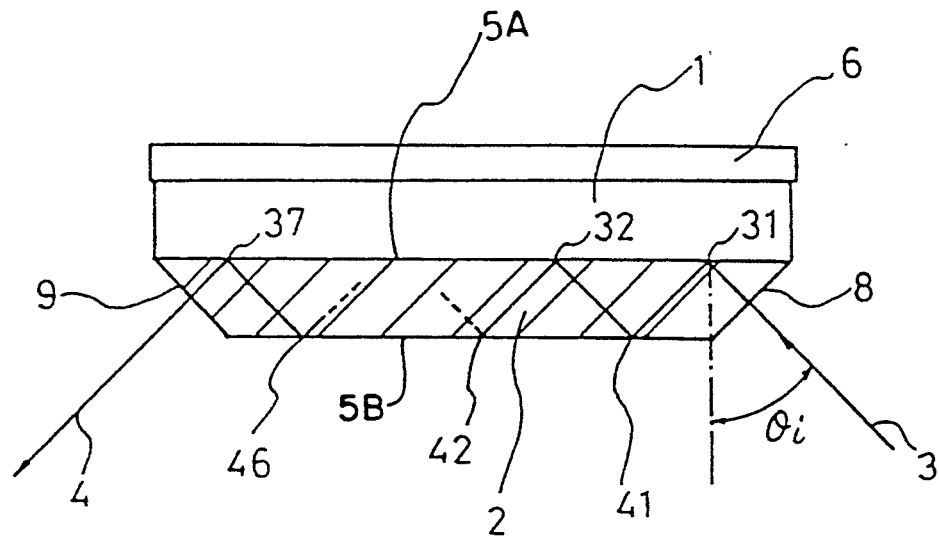
FIG. 1(B) shows a sectional constitution of the portion to be measured and incoming and outgoing infrared rays.

FIG. 1(B) shows a sectional constitution of the portion 11 to be measured of the wafer, and reference numeral 1 is a silicon wafer, which is an object of the measurement, having a highly polished surface. Numeral 2 is a germanium crystal prism selected as an internal reflection element, and 6 is a urethane rubber buffer plate disposed on the back surface of the wafer 1 in order to maintain an airtight contact between the silicon wafer 1 and the internal reflection element 2 which is pushed with the wafer pressured through the buffer plate.

In such a constitution, it is the important point of the experimental example regarding the present invention to select, as the internal reflection element 2, the germanium crystal having a larger refractive index $n_i$, about 4.0 (4.068), than the refractive index ns of silicon, about 3.5 (3.443).

Here, when these refractive indexes ns and $n_i$ are introduced into the formula 1′, the following equation can be obtained:

$$\sin \theta c = (n_s/n_i) = 3.443/4.068 = 0.846$$

$$\theta c = 57° \ 8'$$

The critical angle $\theta c$ is about 57° C. odd. On the other hand, the incident angle $\theta i$ is required to be larger than the critical angle $\theta c$.

The internal reflection element 2 has a boundary surface 5A brought into close contact with the silicon wafer 1, a parallel reflection surface 5B, and an infrared ray incoming surface 8 and an infrared ray outgoing surface 9.

The above-mentioned infrared ray incoming surface 8 and infrared ray outgoing surface 9 are in a mirror symmetry with the normal to the boundary surface 5A by the incident angle $\theta i$, whereby infrared rays 3 and 4 can come and go perpendicularly to the incoming surface 8 and the outgoing surface 9 and the undermentioned function of the present experimental examples can be achieved smoothly.

The size of the silicon wafer 1 to be measured is $10 \times 67$ mm, and its surface roughness is about several Å within 200 Å$^2$.

It is not allowable that dust is present in the boundary surface 5A between the internal reflection element 2 and the silicon wafer 1, and therefore the operation of the close contact should be carried out in a clean room.

In order to secure the reproducibility of the measurement, the silicon wafer 1 is pressed via the buffer plate 6 by means of a spring having a constant compression strength, while the reflection surface 5B of the internal reflection element 2 is pressed against a fixed surface not shown, whereby the internal reflection element 2 is brought into close contact with the silicon wafer 1.

Next, reference will be made to the measurement procedure of the experimental examples.

That is, the infrared ray 3 entered through the incoming surface 8 is reflected at an angle of 90° at a point 31 of the boundary surface 5A, and further reflected at an angle of 90° at a point 41 on the reflection surface 5B opposite to the boundary surface 5A of the internal reflection element 2. Afterward, the infrared ray 3 is similarly reflected at points 32, 42, . . . 46 and 37 in the element 2 seven times in all, and they are radiated through the outgoing surface 9 as the radiant infrared light 4.

The above-mentioned radiant infrared light 4 is then forwarded through the spectrograph 12 to the MCT type detector 13, in which the light 4 is converted to an electrical output corresponding to each wave-number. Afterward, the detection output is Fourier-converted into a spectral line to make a spectrum.

In this case, for the purpose of heightening the precision of calibration, in a blank apparatus having no material to be measured, a blank absorbency RO at each infrared wave-number is previously obtained. Next, a sample is placed in the apparatus, and an absorbency R is then measured, whereby a precise spectrum of a relative absorbency (log R/RO) at each wave-number of the infrared ray can be obtained.

In this experimental example, the incident light is reflected seven times in germanium, as described above, and so the obtained spectrum means average properties at the above-mentioned seven reflection points 31, 32, . . . 37.

Figure 2:
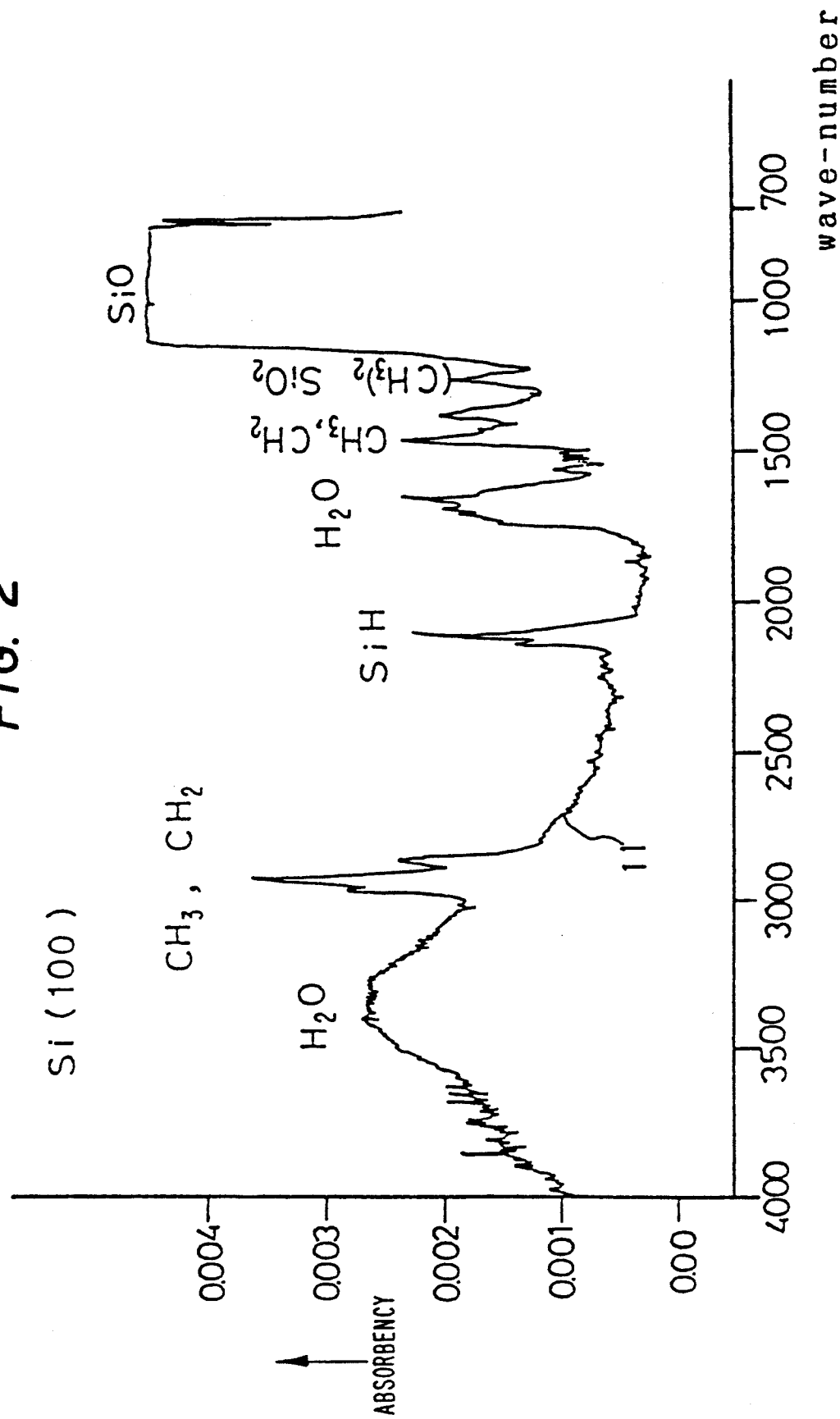
FIGS. 2 to 6 show spectra obtained by measuring the surface states of the silicon wafers in experimental examples regarding the present invention.

FIG. 2 shows a spectrum obtained by measuring the surface state of the silicon wafer in the first experimental example of the present invention, and the abscissa scale stands for a wave-number [cm$^{-1}$] and the ordinate scale stands for a relative absorbency (log R/RO). In FIG. 2, there is denoted the whole range of 2.5 to 14 μm (4,000–700 cm$^{-1}$) which is the transmittable wave length range of germanium used as the internal reflection element 2. A spectrum 11 is the one of a polished (100) surface of an FZ silicon N type wafer washed with a 1.5% hydrofluoric acid solution and then rinsed with pure water.

In the spectrum, an OH stretching vibration and an HOH bending vibration of adsorbed water are seen at wave-numbers of 3,300 cm$^{-1}$ and 1,650 cm$^{-1}$, respectively, and it can be understood that molecular adsorbed water is present even on the hydrofluoric acid-treated surface which is considered to be hydrophobic.

The absorption band peaks of CH$_3$ and CH$_2$ which are organic components are present at wave-numbers of about 2,900 cm$^{-1}$ and about 1,400 cm$^{-1}$, respectively, and an absorption which is supposed to be due to O—(CH$_3$)$_2$Si—O is observed at a wave-number of about 1,260 cm$^{-1}$. They are considered to be reaction products on the surface.

Furthermore, in a spectrum (not shown) in which the range of a wave-number on the silicon (111) surface is from 2,000 to 2,300 cm$^{-1}$, the absorption band of SiH is only present at a wave-number of about 2,080 cm$^{-1}$.

Comparing the spectra of the above-mentioned silicon (111) surface and the silicon (100) surface in FIG. 2, it is apparent that there are many steps of crystal lattice on the (100) surface but there are few steps on the (111) surface, and the latter surface is flat from microscopic observation. Therefore, the flatness of the surface can be evaluated from the fact that the spectrum of the SiH stretching vibration region changes in accordance with the step number in the crystal lattice and it sensitively responds to the peripheral state of SiH.

Figure 3:
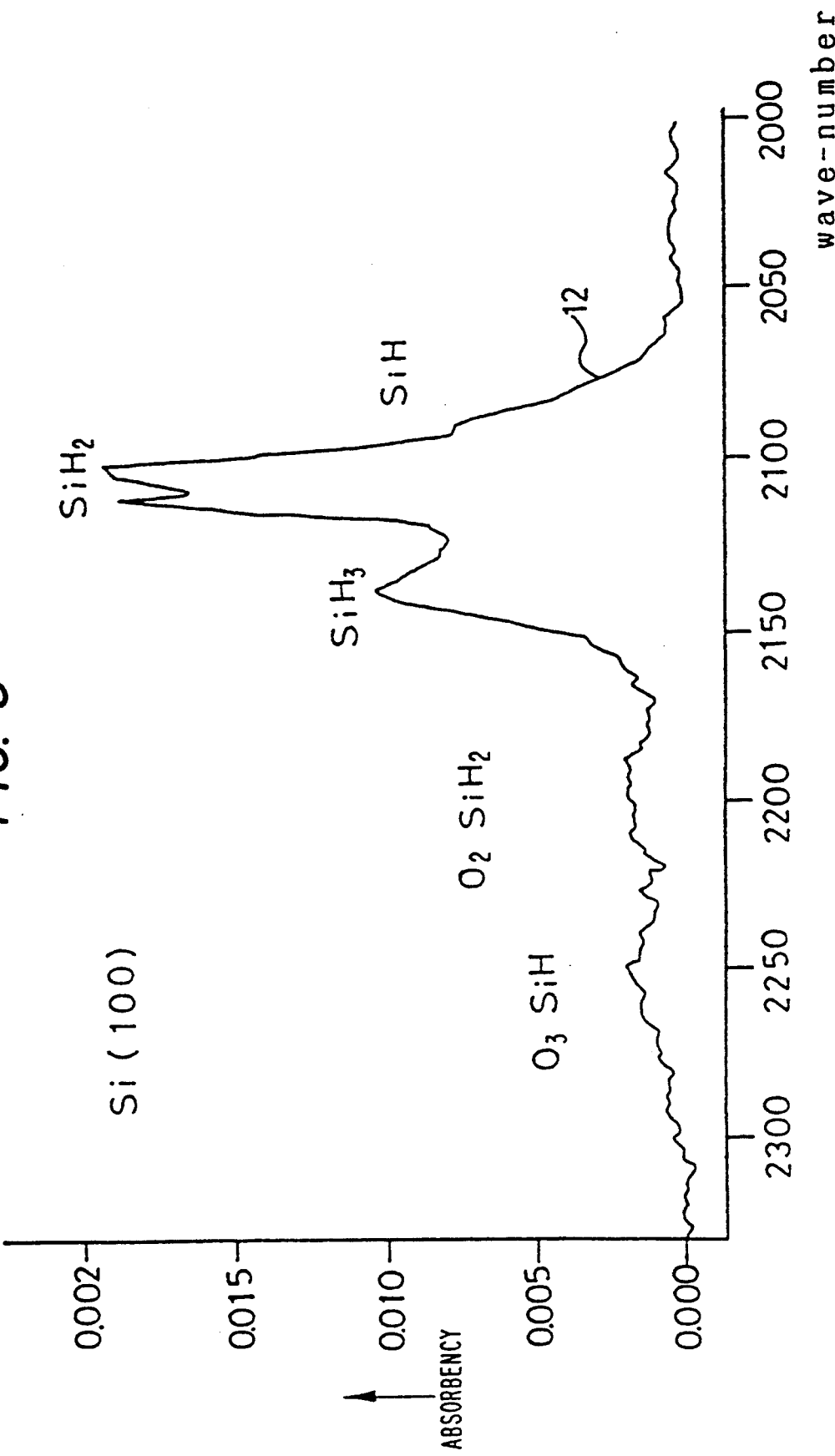

FIG. 3 shows an SiH stretching vibration at a wave-number of about 2,080 cm$^{-1}$ in detail.

Figure 4:
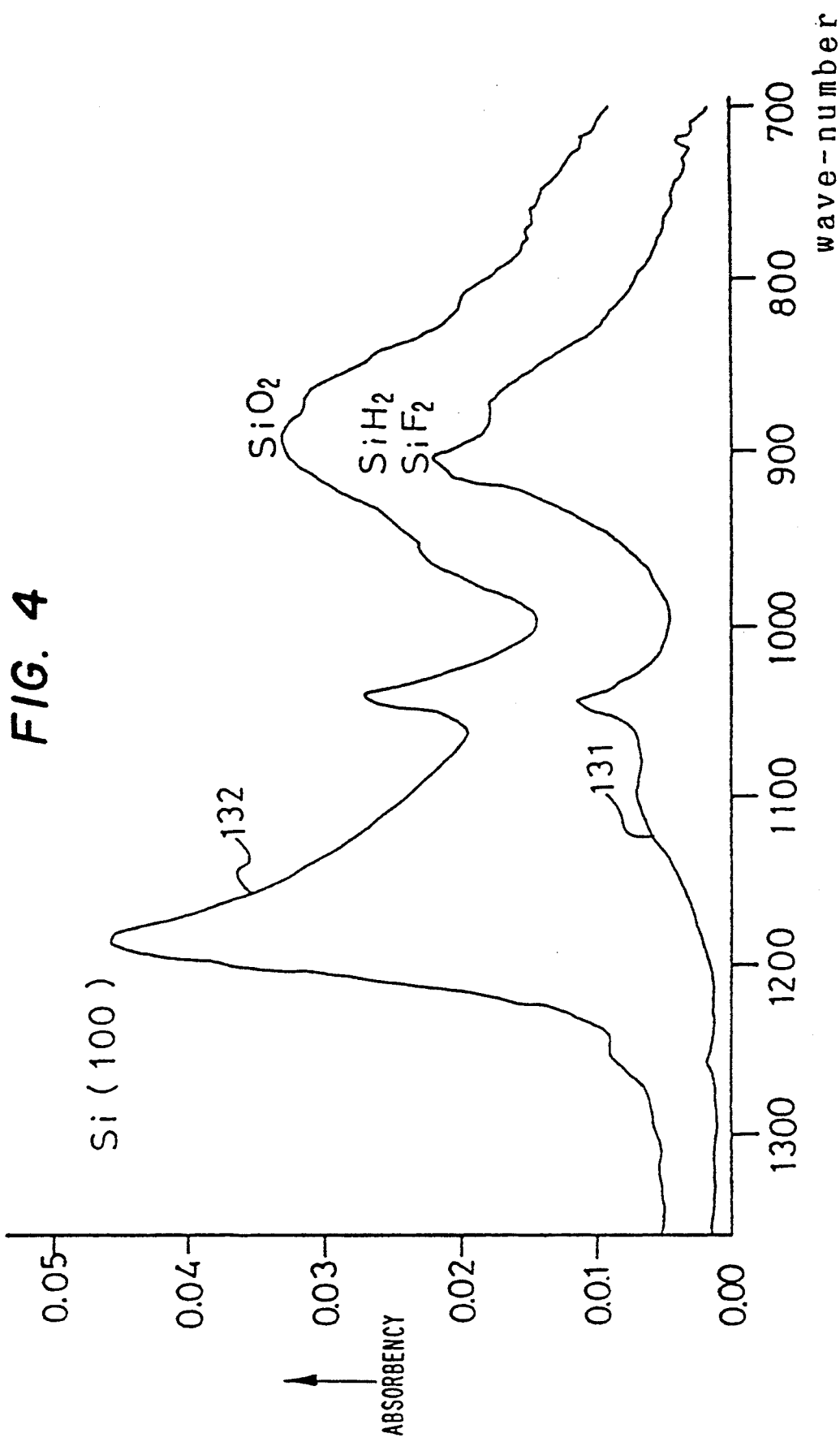
Figure 5:
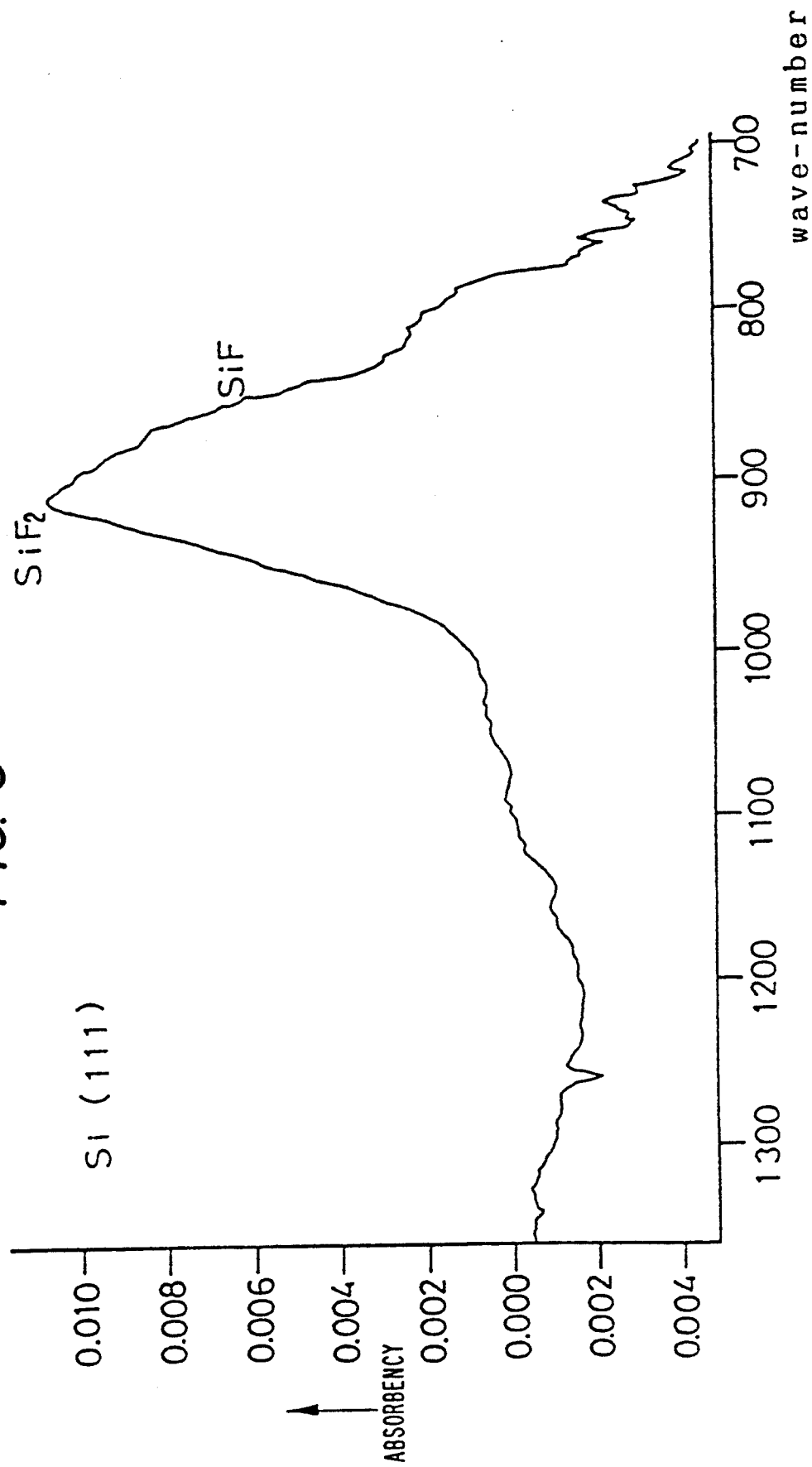
Figure 6:
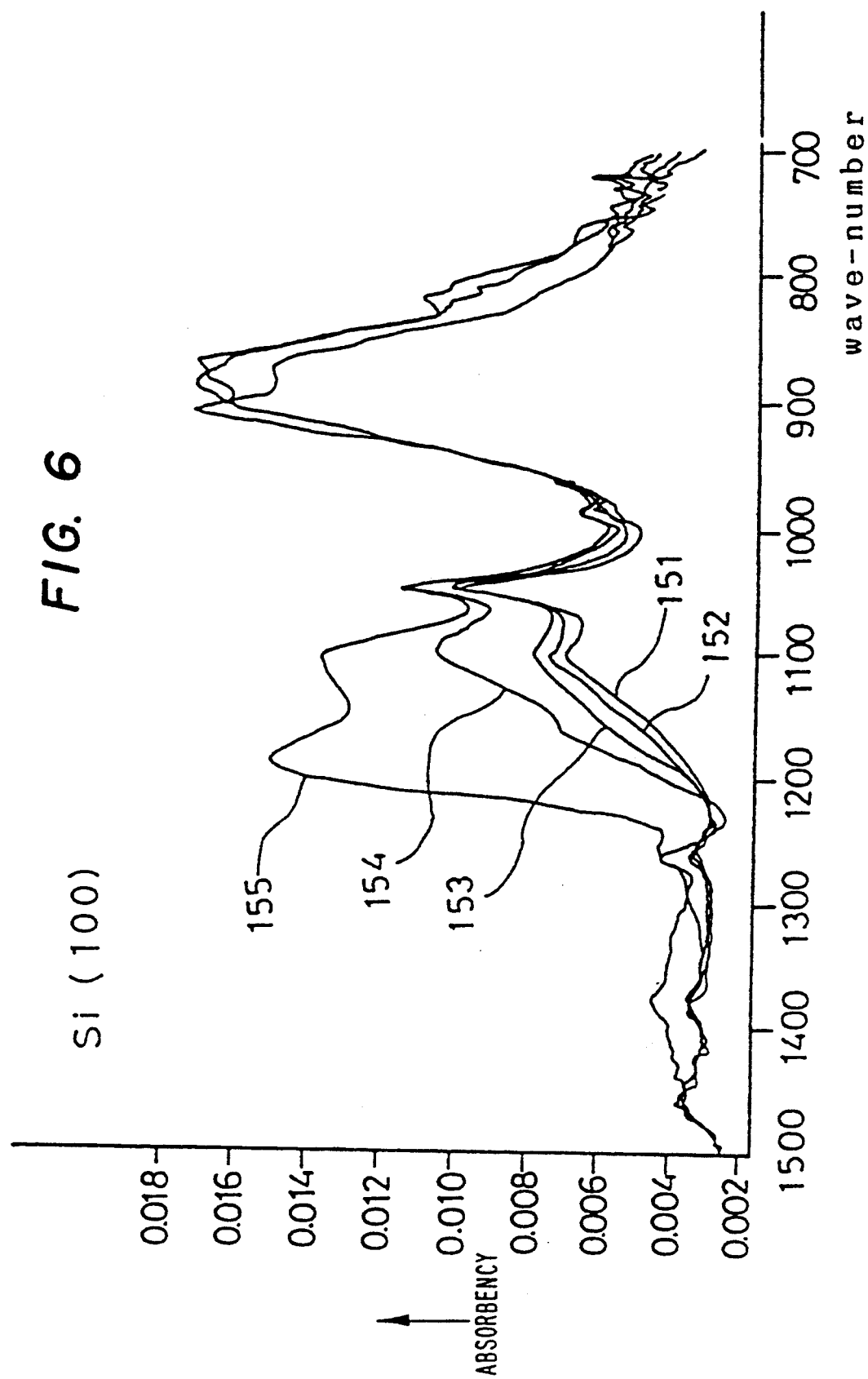
Figure 7:
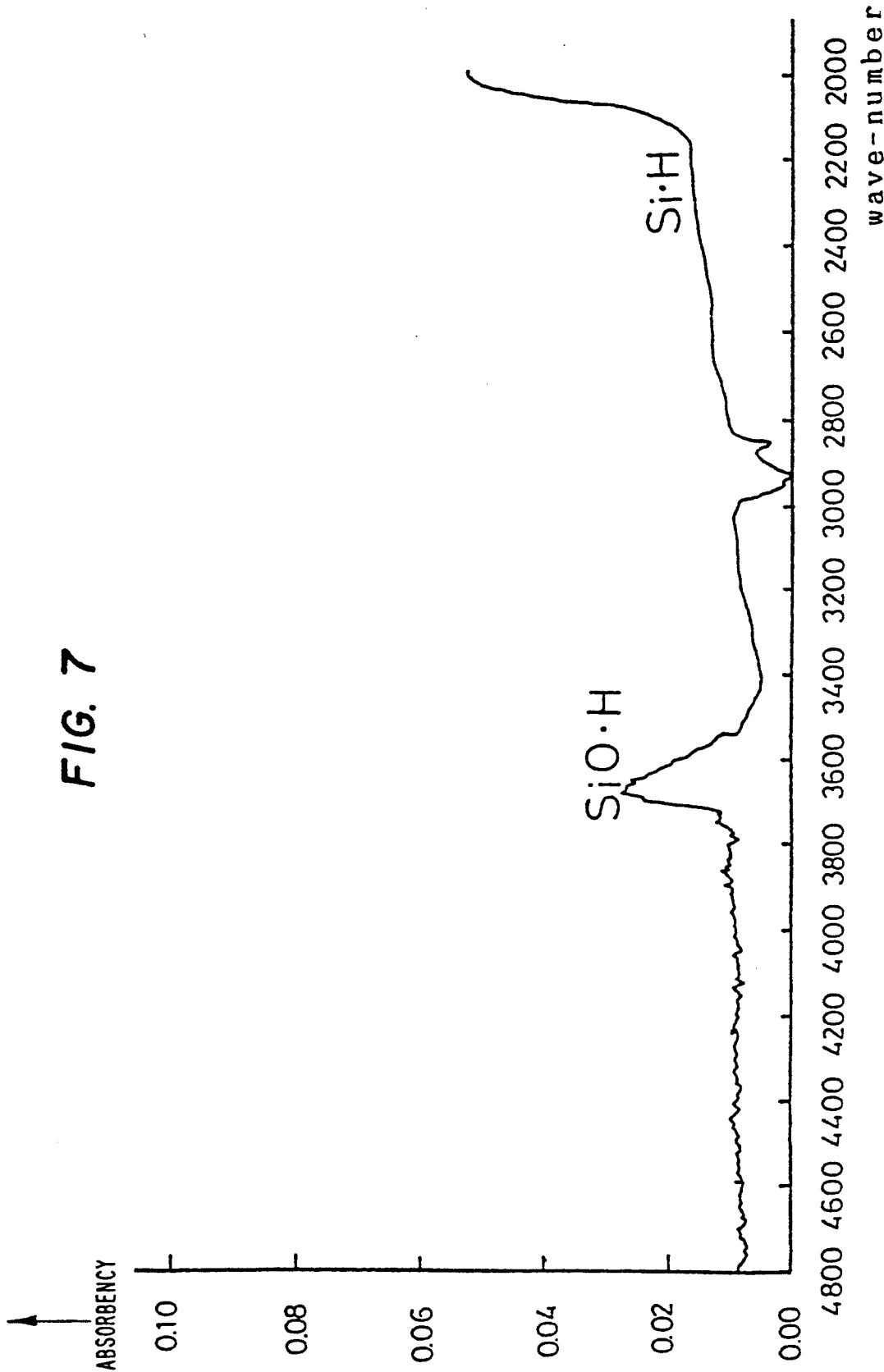
FIG. 7 is a spectrum obtained by measuring the oxide film of a silicon wafer regarding a conventional technique in accordance with an infrared multi-internal reflection method.

FIGS. 4 to 6 show peaks of SiO, SiF and SiF$_2$ present at wave-number of 800 cm$^{-1}$ to 1,200 cm$^{-1}$ in detail.

FIG. 3 shows a spectrum obtained by measuring the surface state of the silicon wafer regarding the second experimental example of the present invention, and a spectrum line 12 mainly elucidates an SiH streching vibration range after the silicon wafer used in the above-mentioned first experimental example has been allowed to stand for 4 hours after washing.

On the spectrum, there are observed absorption bands of $SiH_3$ at a wave-number of about 2,140 cm$^{-1}$, SiH at a wave-number of about 2,080 cm$^{-1}$, $O_2SiH_2$ of an oxidized compound at a wave-number of about 2,200 cm$^{-1}$ and $O_3SiH$ at a wave-number of about 2,250 cm$^{-1}$, in addition to $SiH^2$ at wave-numbers of 2,104 cm$^{-1}$ and 2,115 cm$^{-1}$ expected on the ideal Si (100) surface.

Thus, it can be understood that the above-mentioned measuring method is very sensitive to the surface.

The fact that the bands of $SiH_3$ and SiH are observed in addition to $SiH_2$ means that the surface is not flat from microscopic observation.

Moreover, the fact that the peaks of the oxides $O_2SiH_2$ and $O_3SiH$ are observed at wave-numbers of 2,200 cm$^{-1}$ and 2,250 cm$^{-1}$ respectively means that the silicon atoms with hydrogen are oxidized while the silicon wafer is allowed to stand for 4 hours after the washing.

FIG. 4 shows a spectrum obtained by measuring the surface state of the silicon wafer regarding the third experimental example of the present invention, and in this drawing, there is shown a spectrum 131 of a wafer washed with a 1.5% hydrofluoric acid solution and another spectrum 132 of another wafer washed with an ammonia hydrogen peroxide solution. Both the spectrum elucidate that natural oxide films are formed on the wafers after the washing.

The absorption band of silica $SiO_2$ at a wave-number of about 1,106~1,200 cm$^{-1}$ whose oxygen atoms are no the silicon surface on the spectral line 132 is in contrast to the case of the spectral line 131.

That is, it is apparent that the difference of the washing manners of the silicon wafer results in the difference of the natural oxidation after the washing.

FIG. 5 is a spectrum obtained by measuring the surface state of the silicon wafer regarding the fourth experimental example of the present invention, and in FIG. 5, there is shown the spectrum of a polished (111) surface of an FZ silicon N type wafer washed with a 1.5% hydrofluoric acid solution and then rinsed with pure water. Comparing this spectrum with another spectrum in which the wafer is not rinsed with pure water, it is apparent from the spectrum in FIG. 5 that the amount of SiF is decreased by the rising with pure water.

Chemical species in the wave-number range of 800 to 900 cm$^{-1}$ are SiF at a wave-number of about 830 cm$^{-1}$ and $SiF_2$ at a wave-number of about 920 cm$^{-1}$.

FIG. 6 is a spectrum obtained by measuring the surface state of the silicon wafer regarding the fifth experimental example of the present invention, and spectra 151, 152, ... 155 in this drawing are obtained by allowing samples to stand for 2 hours, 4 hours, 8 hours, 1 da and 12 days after washing with a 1.5% hydrofluoric acid solution.

The feature of FIG. 6 is that the first absorption band peak based on interstitial oxygen in the lattice appears at a wave-number of 1,106 cm$^{-1}$ and a large absorption band appears on the side of a higher wave-number. Judging from the absorption band peak above-mentioned, the oxidation of the wafer surface can be imaged to start by getting into and between the lattice of oxygen. The first absorption band which appears at a wave-number of about 1,150 cm$^{-1}$ on the side of the higher wave-number shifts to a wave-number of about 1,225 cm$^{-1}$. This can be presumed to be due to the fact that the bond angle of Si—O—Si expands.

Although not shown, the NH stretching vibration range of amines is also present at a wave-number of 3,300 cm$^{-1}$, and therefore it can be observed by the measuring manner of the present invention.

What is claimed is:

1. A method for evaluating a surface condition selected from the group consisting of surface roughness, adsorption of molecular water, hydrocarbon or amine impurities, and bonding of hydrogen, fluorine or hydrocarbon groups to silicon atoms of a silicon surface of a silicon wafer said method comprising the steps of bringing an internal reflection element having a larger refractive index than that of silicon into direct contact with said silicon surface, selecting a light source having at least a wave length range which compounds present on said silicon surface can absorb, introducing light having a larger incident angle than a critical angle of the internal reflection element from said light source into said element, whereby light is multiply reflected internally of and then emitted from said internal reflection element, measuring the spectrum of the emitted light, and analyzing the measured spectrum to identify the presence of surface irregularities, adsorbed molecular impurities or terminally bonded atoms or groups on the silicon surface.

2. The method for evaluating the surface state of a silicon wafer according to claim 1 wherein said internal reflection element having a larger refractive index than that of silicon is germanium.

3. The method for evaluating the surface state of a silicon wafer according to claim 2 wherein said light source is an infrared ray in a wave-number range of 4,000 to 700 cm$^{-1}$.

4. The method for evaluating the surface state of a silicon wafer according to claim 2 wherein said internal reflection element has a boundary surface brought into close contact with said silicon wafer, parallel reflection surface, and an infrared ray incoming surface and an infrared ray outgoing surface formed on the opposite sides thereof, and said incoming surface and outgoing surface are in a mirror symmetry with the normal to said boundary surface by an incident angle $\theta i$, whereby an infrared ray can come and go perpendicularly to said incoming surface and outgoing surface.

5. The method for evaluating the surface state of a silicon wafer according to claim 4 wherein said incident angle is in the range of 57° 8' to 90°.

6. A method according to claim 1, wherein said spectrum is measured using a Fourier infrared spectrometer.

7. A method according to claim 1, wherein said method is carried out under an ambient pressure atmosphere.

8. A method according to claim 1, wherein said analyzing step is carried out by comparing peaks of the measured spectrum to reference values indicative of the presence of absorbed molecular impurities or terminally bonded atoms or groups.

* * * * *